United States Patent [19]

Amrani

[11] Patent Number: 5,457,028
[45] Date of Patent: Oct. 10, 1995

[54] STANDARD PLATELET SAMPLES AND METHOD FOR PREPARATION THEREOF

[75] Inventor: David L. Amrani, Glendale, Wis.

[73] Assignee: Milwaukee Heart Research Foundation, Milwaukee, Wis.

[21] Appl. No.: 872,013

[22] Filed: Apr. 22, 1992

[51] Int. Cl.$^6$ .................................................. G01N 33/531
[52] U.S. Cl. ..................... 435/7.21; 435/7.24; 435/7.92; 435/963; 435/967; 436/10; 436/63
[58] Field of Search ............................ 435/7.21, 7.92, 435/7.95, 7.24, 7.5, 967, 963; 436/63, 518, 536, 808, 10

[56] References Cited

U.S. PATENT DOCUMENTS

| | | | |
|---|---|---|---|
| 4,228,237 | 10/1980 | Hevey et al. | 435/7 |
| 4,820,505 | 4/1989 | Ginsberg et al. | 424/9 |
| 5,246,832 | 9/1993 | Michelson et al. | 435/7.21 |
| 5,256,538 | 10/1993 | Aiken et al. | 435/7.21 |

OTHER PUBLICATIONS

Berman et al., Methods in Enzymology 169:314, 1989.
The Role of Fibrinogen Aa Chains in ADP–Induced Platelet Aggregation in the Presence . . . Amrani et al., pp. 919–924 (1988)–Blood, vol. 72, No. 3.

Shattil et al *J. Biol. Chem.* vol. 260, No. 20 pp. 11107–11114, 1985.

M. Wilchek et al, *Immunology Today*, 5, 39–43, 1984.

*Primary Examiner*—David Saunders
*Attorney, Agent, or Firm*—Foley & Lardner

[57] ABSTRACT

A method for determining the activation level of platelets and other types of blood cells that undergo activation by ELISA and other immunoassay techniques includes the step of reacting a sample containing the blood cells in a liquid phase with an excess quantity of an activation-specific primary antibody prior to allowing the cells in the sample to bind to a solid surface. This differs from typical ELISA procedures, wherein the cells are bound to the surface of a plastic test tube or microtiter plate prior to addition of the primary antibody. It has been discovered according to the invention that binding the cells to a surface prior to reaction with the primary antibody changes the activation level of the cells, making the assay less accurate.

15 Claims, 2 Drawing Sheets

STANDARD PLATELET SAMPLES AND METHOD FOR PREPARATION THEREOF

TECHNICAL FIELD

This invention relates to an immunoassay, particularly an enzyme-linked immunoabsorbent assay (ELISA) for monitoring activation of platelets and other types of blood cells which undergo activation.

BACKGROUND OF THE INVENTION

In the past five years, the use of fluorescent-activated flow cytometry with specific activating antibodies has allowed investigators to directly monitor platelet activation and subsequent microaggregate formation. While accurate and specific, flow cytometry is extremely expensive, requiring an expensive machine and maintenance, and a dedicated technician. Platelet assay methods using other well-known assay systems, such as ELISA, radioimmunoassay (RIA) and Western blot analysis have been described in Berman et al., *Methods in Enzymology* 169:314, 1989. Berman et al. discuss an ELISA assay which involves fixing platelets and placing the fixed platelets directly in a microtiter plate for the purpose of screening for activation specific antibodies.

Current assays for monitoring platelet activation in patients who may be at risk for thrombosis or thrombosis-related conditions involve indirect assessment of this activation by measuring systemic released platelet products (factors present in the circulation). Such products include platelet factor 4 and β-thromboglobulin, or the thromboxane $B_2$, a stable product of platelet activating factor thromboxane $A_2$. Unfortunately, circulating levels of these factors can undergo metabolically-produced changes, and as such these factors are considered indirect measures of platelet activation. As such, a need remains for a direct platelet activation assay which can be carried out on patient samples without undue complexity or expense.

SUMMARY OF THE INVENTION

A method according to the invention for determining the activation level of blood cells by an immunoassay of the type wherein a primary antibody undergoes specific binding with the blood cells and a labelled secondary antibody undergoes specific binding with the primary antibody-blood cell complex, such as ELISA, includes the step of reacting a sample containing the blood cells in a liquid phase, e.g. an aqueous suspension, with an excess quantity of an activation-specific primary antibody prior to allowing the cells in the sample to bind to a solid surface. This differs from typical ELISA procedures, wherein the cells are bound to the surface of a plastic test tube or microtiter plate prior to addition of the primary antibody. It has been discovered according to the invention that binding the cells to a surface prior to reaction with the primary antibody changes the activation level of the cells, making the assay less accurate.

The activated platelet ELISA assay of the invention is a relatively simple procedure for quantitation of the amount of activated platelets in the bloodstream of patients who may be at risk for thrombosis or thrombosis-related conditions. Accordingly, a method for controlling the activation level of platelets or other blood cells in a patient's bloodstream according to the invention involves the steps of obtaining a sample of platelets or other blood cells which undergo activation, immunoassaying the sample with an antibody that selectively binds to activated platelets or other blood cells while the sample remains in liquid suspension, correlating the results with a standard to determine the degree of activation of the platelets or cells prior to the assay, and administering a drug to the patient in an amount effective to maintain activation at a predetermined level. For platelets, if the assay reveals an elevated level of activation, the physician then administers an anticoagulant or antiplatelet agent or increase the anticoagulant or antiplatelet agent dosage. If the opposite is true, the anticoagulant or antiplatelet agent dosage can be decreased.

According to a preferred aspect of the invention, the assay includes the steps of:

(A) obtaining a sample of platelets from a living subject;

(B) adding an excess quantity of a platelet activation-specific primary antibody to the platelets in an aqueous suspension and allowing the primary antibody to react with the platelets for a time sufficient to allow substantially complete specific binding between the antibody and activated platelets;

(C) forming a complex between the platelets bound to the primary antibody and, a secondary antibody bound to an enzyme, in which the secondary antibody reacts by specifically binding to the primary antibody;

(D) adding a substrate to the platelet complexes, which substrate reacts with the enzyme to produce a visible indicator;

(E) measuring the extent to which the visible indicator is present; and (F) correlating the results with a standard, such as a standard curve, to determine the degree of activation of the platelets prior to the assay. For purposes of the invention method, an "excess" quantity is an amount sufficient to react with all of the available binding sites.

In one embodiment, step (C) further comprises adding a labelled secondary antibody to the suspension which reacts with and specifically binds to the primary antibody. The label is one of a pair of specific binding substances, such as biotin, which binds specifically to the other substance, such as streptavidin. The platelets are separated from unbound labelled secondary antibody, and an enzyme labelled with the other of the pair of specific binding substances is added to the platelets so that the enzyme becomes bound to the secondary antibody. The platelets are then separated from unbound enzyme. In the alternative, the secondary antibody may be linked to the enzyme in advance, and the resulting complex reacted directly with the platelet having primary antibody bound thereto.

The invention further contemplates a kit for carrying out the assay of the invention. The kit includes necessary reagents, including standards containing fixed platelets activated at different, predetermined levels for generating a standard curve, and the necessary primary and optionally secondary antibody preparations, as well as written directions giving a protocol for carrying out the assay.

BRIEF DESCRIPTION OF THE DRAWINGS

The drawings are graphs of experimental results on a semi-logarithmic scale, wherein.

DETAILED DESCRIPTION

Figure 1:
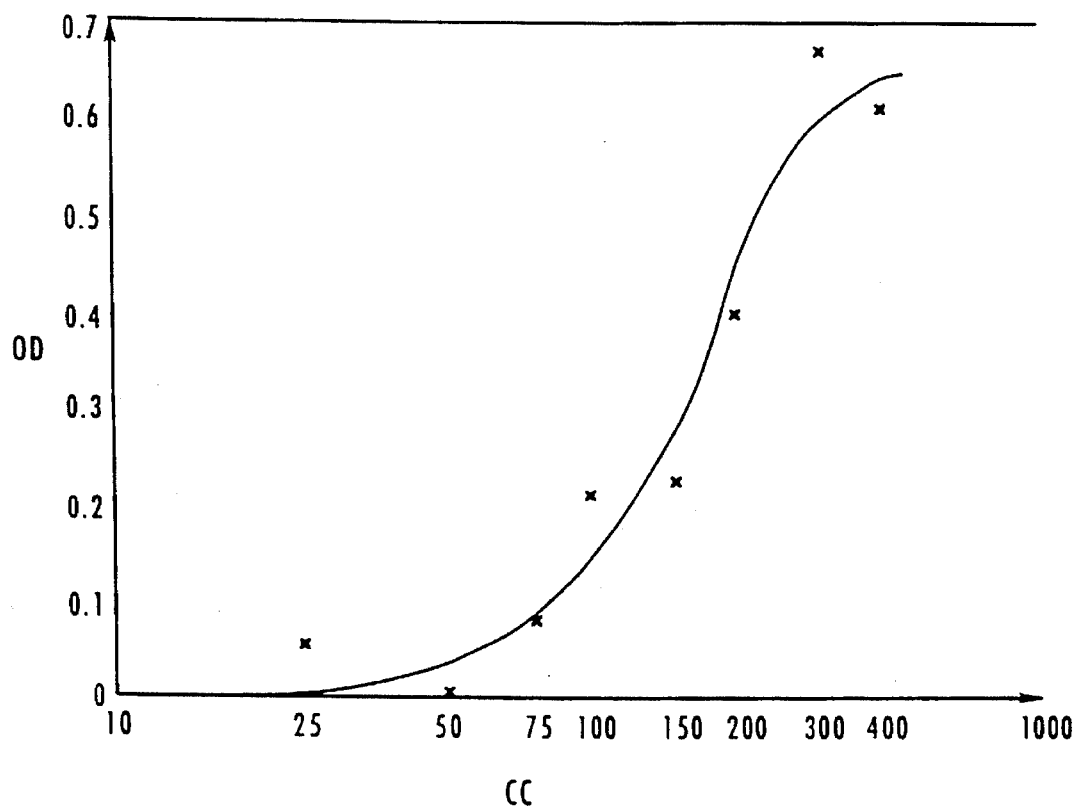
FIGS. 1 and 2 are plots of optical density (OD) against collagen concentration (CC) in μg/ml for two examples of assays according to the invention.

The assay of the present invention can eliminate the need for any equipment other than that commonly found in an ordinary clinical/or research laboratory. The following description deals with a platelet assay, but the procedure is also applicable to samples of other types of cells which undergo activation, for example, blood cells other than red blood cells, such as monocytes, lymphocytes, and granulocytes.

The invention is based in part on the discovery that affixing platelets or the associated primary antibody that binds thereto to a plastic surface as part of the ELISA assay causes surface activation of the platelets, rendering the assay inaccurate. This effect is most pronounced for plastics which have a substantial electrical surface charge, such as polyethylene and polystyrene. However, it has been discovered that an ELISA assay for platelet activation can be carried out if binding of the primary antibody occurs in aqueous suspension. In practice, this means taking care to avoid binding the platelets to a plastic surface, such as the bottom of a microtiter well, until after the platelets have reacted with the primary antibody. Accordingly, according to the assay of the invention, the platelet suspension is placed in a plastic microtiter well or test tube but not centrifuged until after the reaction between the primary antibody and the platelets has taken place.

In accordance with one embodiment of the assay method, platelets are obtained from whole blood by standard centrifugation procedures, for example, using a standard laboratory centrifuge at room temperature and spinning for 15 minutes at 350 times gravity (xG). The assay can be performed with either platelet-rich plasma, or washed platelets. The procedure for washing the platelets may be the one described in Amrani et al., *Blood*, Vol. 72, No. 3, 1988, pp. 919–924, the contents of which are incorporated by reference herein. In preparing platelets taken from normal individuals for use as standards, washed platelets are preferred to provide better uniformity in the results. For the patient (unknown) sample to be measured, the procedure may be simplified by using platelet-rich plasma. After washing, the platelets are then resuspended in a buffer solution at a pH of about 7.3 to 7.4. In general, buffer solutions according to the invention are formulated to maintain the platelets in a stable condition by maintaining salt concentrations and pH at normal plasma levels.

A calcium inhibitor, e.g., a chelating agent such as ethylenediaminetetraamine (EDTA) or citrate, is preferably added to the platelet suspension prior to activation. The calcium inhibitor is added in an amount effective to chelate substantially all calcium ions in the aqueous suspension so that calcium does not bind to FC receptors on the platelet surface, leading to unwanted binding of S12 antibody containing FC regions of the antibody at these sites. The amount of calcium inhibitor added is generally in the range of 2 to 10 mM in the suspension.

The platelets are then activated at room temperature with one of a number of known agonists such as thrombin (for washed platelets only) in an amount ranging from 0 units/ml to 1.0 units/ml, or collagen (for either platelet-rich plasma or washed platelets) in an amount ranging from 0 µg/ml to 400 µg/ml. A specific primary antibody which is directed at platelet-activation specific antigens (receptors) is also added, and the mixture is allowed to react for a time sufficient to allow the binding reaction to go to substantial completion, generally 30–60 minutes. Suitable primary antibodies include S12 or CD63, and others which are commercially available. CD63, available from AMAC Inc., Westbrook, ME binds to glycoprotein (GP) 53 lysosomal protein. Antibody S12, described in McEver and Martin, *J. Biol. Chem.* 259, 9799 (1984), is directed against granule membrane protein 140.

After the antigen-antibody reaction has proceeded to completion, one or more inhibitors of platelet activation are then optionally added to minimize further activation and antibody binding. Such inhibitors include prostaglandin E1 ($PGE_1$), preferably used in an amount of 5 ng to 100 ng per ml of carrier liquid, preferably ethanol, typically 10 ng/ml ethanol, and hirudin, a specific thrombin inhibitor used at the same concentration as thrombin.

A secondary antibody is added to link to the platelet-attached primary antibody (i.e., the activation-specific antibody). The secondary antibody is generally either coupled in advance with an enzyme, as in Example 1 below, or else is labelled with a substance such as biotin. In the latter embodiment, a biotin-labeled anti-mouse immunoglobulin, preferably goat or rabbit anti-mouse Ig depending on the antibody used, is added to link to the platelet-attached primary antibody. The reaction is allowed to proceed in the mixture for a sufficient time, typically 30–60 minutes.

The platelet-antibody mixture is then separated by centrifugation from a supernatant material containing any antibody remaining unbound either directly, or through a dense medium such as sucrose or silicone oil. Centrifugation time may vary from about 2 seconds to 10 minutes depending on the medium used. For example, a 6 minute spin at 10,000 xG is preferred for a 5:1 silicone-oil mixture for washed platelets, and 8 minute spins at 10,000 xG are used for 8:1 silicone-oil mixture.

The platelet pellet is then washed 1 to 6 times with buffer, and an enzyme bound to streptavidin, such as streptavidin peroxidase, is added and allowed to react for 15–60 minutes. Avidin is a molecule that binds specifically and with high affinity to biotin. Preferred enzymes include peroxidase and alkaline phosphatase. If the enzyme is pre-linked to the secondary antibody as in Example 1 below, then the use of labels (specific binding substances) such as biotin and streptavidin may be omitted, along with the associated separation steps. The label for the secondary antibody could also be a fluorescent label, radioactive label such as $^{125}I$, or other suitable marker substance. However, an enzyme suitable for ELISA has proven practical and sensitive, and is preferred.

After the reaction period, the pellet is again washed, e.g. 2–6 times, and a substrate such as 2,2-azino-di(3-ethylbenzylthiazoline) sulfonic acid (ABTS) is added to the pellet to develop the color. The samples are removed from the tubes and placed in a microtiter plate, and absorbance is read at a standard wavelength.

The foregoing procedure is used to construct a standard curve by activating platelets to predetermined levels based on the amount of activating agent used. The procedure can then be repeated without prior in vitro activation to determine activation levels for unknown samples. In assaying the unknown (patient) sample, it is preferred to use platelet-rich plasma; the washing procedure is accordingly omitted. Whole blood is centrifuged at a relatively low speed, e.g. 350 xG, to obtain platelet-rich plasma. The steps of adding the activator and inhibitor are likewise omitted. Otherwise, the procedure remains substantially the same. The activation level of the unknown sample is then read from the linear portion of the standard curve.

In the foregoing procedure, each successive step is preferably carried out with the platelets remaining in the same tube or microtiter well. Since polypropylene has less surface charge and less tendency to cause the platelets to bind thereto spontaneously, use of a polypropylene microtiter plate, particularly a Nunc pre-siliconized polypropylene microtiter plate, is most preferred.

With a sufficiently large pool of platelet samples from different donors, it is believed that a generalized standard curve could be developed. Accordingly, instead of generating a standard curve for each determination, the standard according to the invention may be a predetermined standard curve that correlates activation level with the observed color change, fluorescence or similar indication.

In either embodiment, the invention provides a method for identifying patients who may be at risk for thrombosis or thrombosis-related conditions, such as artificial heart recipients. Anticoagulant or antiplatelet drugs are commonly administered to such patients. In a method for prevention of thrombosis according to the invention, the assay of the invention is carried out on a patient, such as a person on anticoagulant or antiplatelet drug therapy, and the activation level is compared to a normal activation level. The latter is generally around 5–6%, i.e., in a normal person only 5 to 6 percent of platelets will be activated at any given time. In the patient, who may be on anticoagulant drug therapy, the activation level may become as high as 25–50%; 5 to 10 times the normal level. This can be readily determined by, for example, carrying out the assay of the invention on several normal individuals and comparing the values obtained on the standard curve with that of the patient.

When the assay reveals that the activation level is excessively high, for example, over 25%, the dosage of the anticoagulant drug can be increased, a stronger anticoagulant can be used, or the like. Correspondingly, if the assay indicates that activation level is too low, for example, below 5%, then the dosage of the anticoagulant drug can be decreased, or a weaker anticoagulant can be used. Such a method can thereby prevent strokes and similar complications by detecting elevated platelet activation and permitting remedial drug therapy before clotting actually occurs. Percent activation can be correlated through clinical trials to the optical density determined by the assay, the relationship being roughly linear.

The immunoassay used in the method for controlling platelet or other blood cell activation according to the invention need not be the primary and secondary antibody-based assay described above. Any suitable assay system could be used, for example, standard radioimmunoassay or immunofluorescence procedures, so long as the assay is conducted in the fluid phase so that the result of the assay accurately reflects the activation level of the cells in the patient's bloodstream. For example, the primary antibody could be directly labelled with an enzyme, fluorescent label, radioactive isotope or similar label, and the secondary antibody could be omitted.

The following examples further illustrate the invention:

EXAMPLE 1

The following solutions were prepared. In each case, sufficient water was added to the listed ingredients to bring the volume of the solution to the level indicated:

| ACD Anticoagulant: | |
|---|---|
| Citric acid (MW = 210.14) | 0.80 gm |
| Sodium citrate (MW = 357.16) | 2.20 gm |
| Dextrose (MW = 180.16) | 2.45 gm |
| Distilled H$_2$O | to 100 ml |
| Wash Buffer: | |
| 108 mM NaCl (MW = 58.44) | 3.16 gm |
| 38 mM KCl (MW = 74.56) | 1.42 gm |
| 1.7 mM NaHCO$_3$ (MW = 84.01) | 0.071 gm |
| 21.2 mM Na$_3$ citrate (MW = 294.10) | 3.12 gm |
| 27.8 mM sucrose (MW = 342.30) | 4.76 gm |
| 2.35 mM MgCl$_2$-6H$_2$O (MW = 203.31) | 0.112 gm |
| Distilled H$_2$O | to 500 ml |

Buffer pH was adjusted to 6.5 by titration of the solution with 1 N NaOH. PGE$_1$ and apyrase were added as needed to inhibit activation. For 10 ml wash buffer, 21.2 μl PGE$_1$ solution, 3.5 μg/ml and 25 μl, 1.25 units/ml apyrase were used; for 20 ml wash buffer, the amounts were 42.3 μl PGE$_1$ and 50 μl apyrase.

| Platelet Resuspension Buffer: | |
|---|---|
| 137 mM NaCl (MW = 58.44) | 2.00 gm |
| 2 mM KCl (MW = 74.56) | 0.05 gm |
| 0.3 Mm NaH$_2$PO$_4$.H$_2$O (MW = 137.99) | 0.02 gm |
| 2 mM CaCl$_2$.2H$_2$O (MW – 147.02) | 0.07 gm |
| 1 mM MgCl$_2$.6H$_2$O (MW – 203.31) | 0.05 gm |
| 5.5 mM dextrose (MW = 180.16) | 0.25 gm |
| 5 mM HEPES (MW = 238.30) | 0.30 gm |
| 12 mM NaHCO$_3$ (MW = 84.01) | 0.25 gm |
| 0.35% BSA (add just before use) | 0.875 gm |
| Distilled H$_2$O | to 250 ml |

HEPES is an amine commercially available from Sigma. Buffer pH was adjusted to 7.3–7.4 by titration of the solution with 1 N NaOH. PGE$_1$ is added as needed to inhibit activation, here in an amount that provided a final concentration of 5 ng/ml.

Pre-siliconized polypropylene Eppendorf tubes were filled with 0.5 ml of silicone oil. The silicone oil was a 5:1 mixture of HIPHENYL DC-550 silicone oil to methyl DC-200 silicone oil. Fresh blood was collected into 15 ml Vacutainer tubes containing 2.14 ml ACD anticoagulant in a ratio of 9 parts by volume blood to 1 part ACD. Washed platelets were then prepared from the blood samples. Blood was drawn into the prepared VACUTAINER tubes and centrifuged at 800 rpm (350 xG) for 15 minutes in an IEC-CENTRA-7 tabletop centrifuge. The platelet-rich plasma was carefully removed from the red cell layer and placed into a clean 13 ml polypropylene tube. 5.75 ml of platelet-rich plasma was obtained, to which 8.22 μl of PGE$_1$ inhibitor solution was added to yield a final concentration 5 ng prostaglandin E$_1$ per ml of combined solution. PGE$_1$ solution used in this example contained 3.545 μg of prostaglandin E$_1$ per ml of 100% ethanol.

The platelets were then pelleted by centrifugation at 700 xG for 5 minutes. The platelet-poor plasma supernatant may be saved as a source of fibrinogen for a platelet aggregation assay, or may be discarded. The platelet pellet usually contains red cells. The platelets were carefully resuspended in wash buffer containing inhibitors, as described above, at one half the original volume of the platelet-rich plasma. Platelets were removed only from around the red cells at the center, and the red cells were discarded.

The platelets were centrifuged at 1500 rpm (500 xG) for 5 minutes to pellet the platelets. The supernatant was poured off, and the platelets were resuspended in the wash buffer and inhibitors. The platelets were then centrifuged again at 500 xG for 5 minutes. The supernatant from the second wash was discarded, and the platelets were resuspended in the wash buffer containing inhibitors. A 0.5 ml sample of the washed platelet suspension was removed to a 4 ml polypropylene tube for counting. Platelet count is platelets/ml times total ml. The platelets were then centrifuged again at 500 xG for 5 minutes. The supernatant from the third wash was discarded, and the platelets were resuspended in platelet resuspension buffer containing no inhibitors.

During the final wash, the platelet count was adjusted to 175,000 platelets per microliter to provide a final concentration of 100,000 platelets/microliter. Then, EDTA was added to the final suspension of platelets to provide a final concentration of 1 mM (millimole). A 200 microliter sample of the washed platelets was pipetted into a number of reaction tubes. Collagen from BioData was reconstituted with distilled water to yield 1.9 mg collagen/ml. 63.2 microliters of the reconstituted collagen suspension were pipetted into each reaction tube to provide final collagen concentrations of 0, 25, 75, 100, 150, 200, 250, 300, 350, and 400 micrograms/mi. 36.8 microliters of S12 antibody solution were then gently pipetted into each tube in amounts to provide a final concentration of 2.0 micrograms of the antibody per ml. Prior to addition, the S12 antibody was centrifuged at the top speed of the microcentrifuge (10,000 xG) about for 15 minutes to remove microaggregates. The reaction tubes were allowed to incubate at room temperature for 30 minutes.

25 microliters of $PGE_1$ solution and 25 microliters of goat anti-mouse IgG heavy and light chains coupled to horseradish peroxidase (GAM IgG(H & L)-HRP, obtained commercially from BioRad) were pipetted into each reaction tube. The GAM IgG(H & L)-HRP contained 0.9 mg/ml IgG and 0.6 mg/ml peroxidase. The $PGE_1$ solution contained $PGE_1$ in an amount calculated to provide a final concentration of 10 ng/ml in the reaction tubes, and the GAM IgG(H & L)-HRP solution was used at a final dilution of 1:300. The GAM IgG(H & L)-HRP was centrifuged before use for 15 minutes to remove microaggregates in the same manner as for the S12 antibody. The reaction tubes were then incubated for 60 minutes as room temperature.

After incubation, 100 microliters from each tube were layered onto the previously prepared silicone oil aliquots in triplicate using wide-bore pipette tips. All tubes were then centrifuged at the top speed of the microcentrifuge (10,000 xG) for 6 minutes at room temperature. The tubes were then decanted. The peroxidase substrate, activated ABTS, was then added to each tube in an amount of 100 microliters per tube, and the tubes were allowed to incubate at 37° C. in the dark for 45 minutes. ABTS development was then stopped by addition of 2 mM sodium azide solution (50 microliters per tube).

Figure 2:
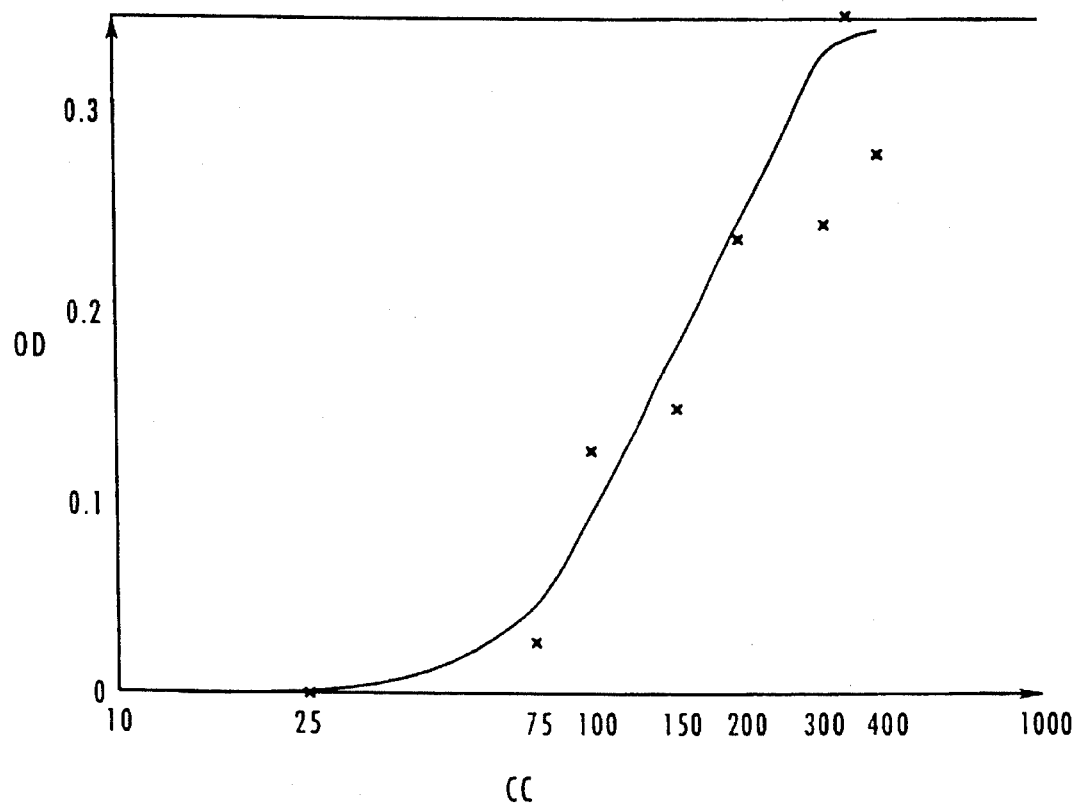
Figure 3:
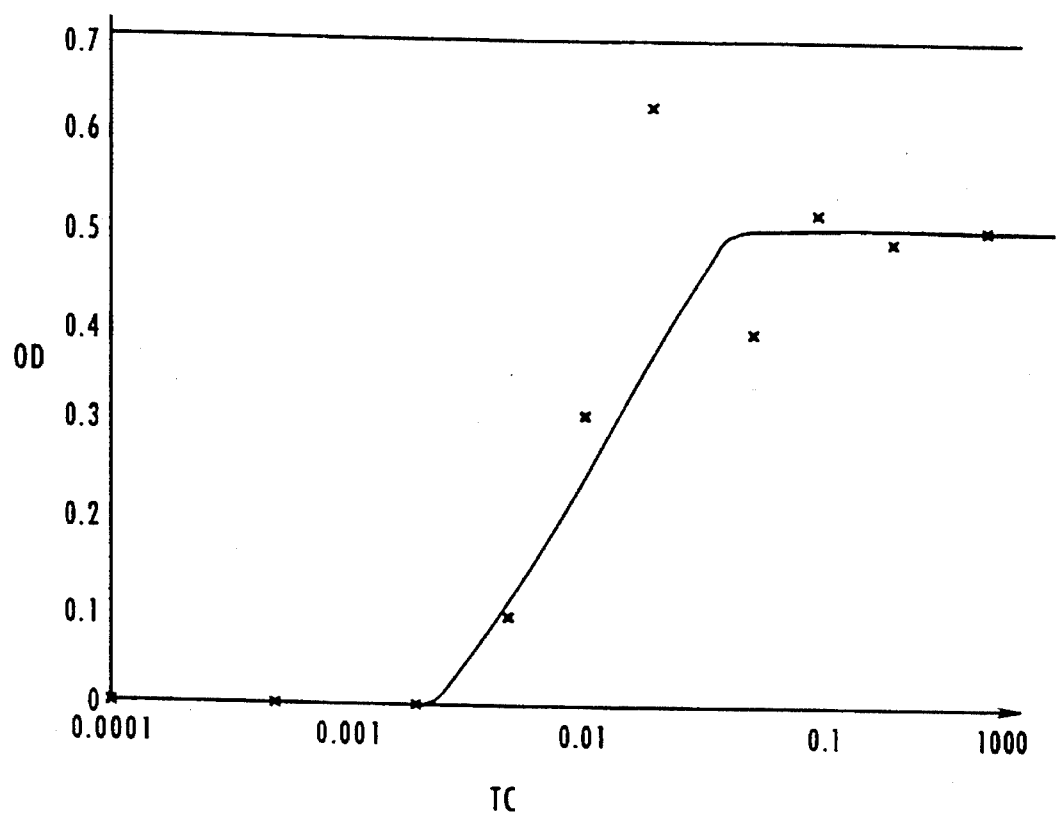
FIGS. 3 and 4 are plots of optical density (OD) against thrombin concentration (TC) in μg/ml for two examples of assays according to the invention.
Figure 4:
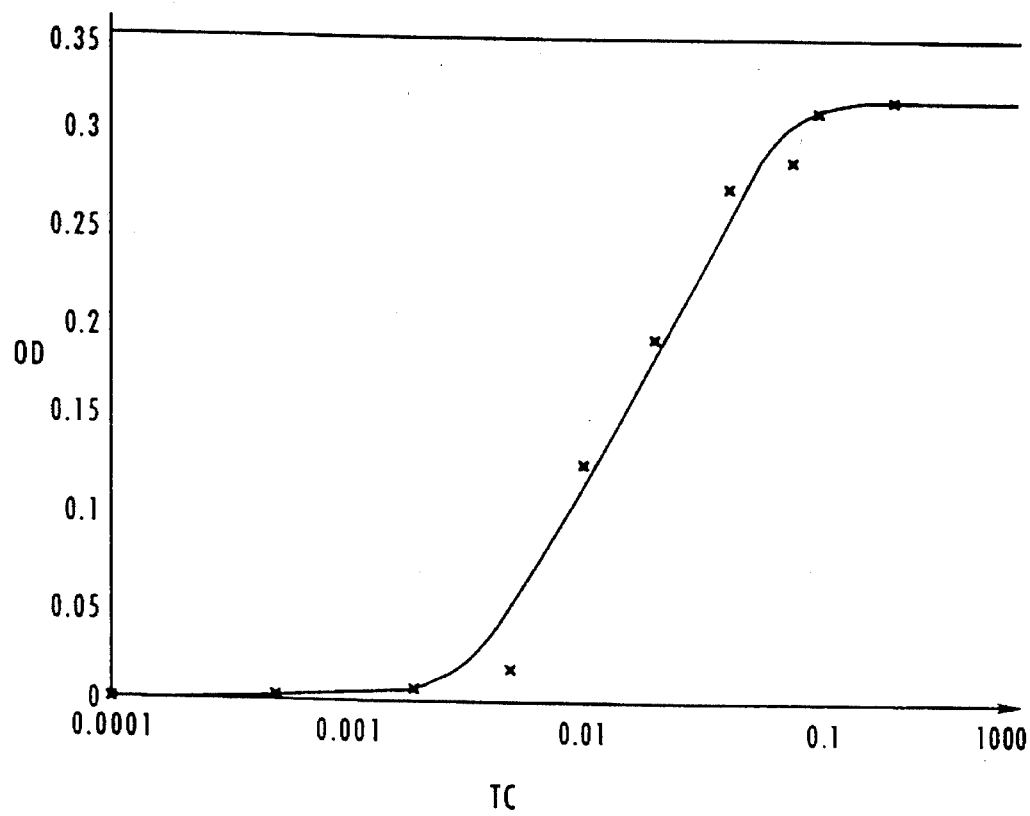

Optical densities were then read for each tube using a Microelisa reader for absorbance at 405 nm. The results are plotted on a semi-log scale in FIGS. 1 and 2. Both represent results for platelets from two normal individuals pooled together. Similar results were obtained using thrombin in concentrations varying from 0 to 1.0 units/ml, as shown in FIGS. 3 and 4. Assay conditions for FIGS. 3 and 4 were 100,000 platelets/ml, 1 mM EDTA, 2 micrograms/ml S12, GAM IgG(H & L)-HRP diluted to 1:300, ABTS as substrate. FIG. 3 represents a single normal donor, whereas FIG. 4 represents platelets from four normal donors pooled together.

FIG. 4 shows much less uncertainty and a more linear plot than FIG. 3. The four graphs together show that greater convergence occurs as the number of individuals contributing to the platelet pool increases. Accordingly, the standards for use in the present invention are preferably prepared using platelets pooled from several (4 or more) individuals. It should also be possible according to the invention to generate a standard curve from a large number of individuals that can be used as a general standard, potentially eliminating the need to generate a new standard curve each time the assay is performed.

EXAMPLE 2

The following illustrates preparation of fixed platelets for use in a kit according to the invention. Platelets were prepared in accordance with Example 1, except as follows. After activation, the platelets were treated with 1% para-formaldehyde in phosphate-buffered saline (100 millimolar sodium phosphate, 150 millimolar NaCl, pH 7.4) for 5 minutes at room temperature. The platelets were spun down by centrifugation, washed 3 times, then counted. After the third spin, the platelets were resuspended in platelet resuspension buffer containing 5% dimethyl sulfoxide (DMSO) at a concentration of $10^9$ platelets per ml. The platelets were then stored for 1 day at $-70°$ C. Samples were then thawed out using a water bath at 37° C.

The procedure of Example 1 was then followed as described above using the thawed platelets. The results were substantially the same as shown in FIGS. 1–4, except that the background level, reflected as the baseline of the graph from the X-axis, was somewhat higher. This example indicates that platelets for use as standards in a kit according to the invention can be prepared in advance and stored frozen until the time of use.

It will be understood that the foregoing description is of preferred exemplary embodiments of the invention, and that the invention is not limited to the specific forms shown. Modifications may be made in the design of the assay without departing from the scope of the invention as expressed in the appended claims.

I claim:

1. A set of separate standard platelet samples each containing fixed platelets activated at different, predetermined.levels, which levels are selected to provide values suitable for preparation of a standard curve using the standard platelet samples, wherein each standard platelet sample consists essentially of the fixed platelets and an aqueous medium, and the platelets Of each standard platelet sample has been removed from blood of a normal individual as platelet-rich plasma or as washed platelets, activated using a different amount of an agonist for each standard platelet sample, then fixed using an effective amount of a fixing agent, and then frozen in an aqueous medium.

2. The set of claim 1, wherein the fixing agent is 1% para-formaldehyde.

3. The set of claim 1, wherein the aqueous medium is a platelet resuspension buffer formulated to maintain the platelets in a stable condition by maintaining salt concentrations and pH at normal plasma levels.

4. The set of claim 1, wherein the platelets have been separated from whole blood, washed, and then suspended in the aqueous medium prior to being activated and fixed.

5. The set of claim 4, wherein the aqueous medium is a platelet resuspension buffer formulated to maintain the platelets in a stable condition by maintaining salt concentrations and pH at normal plasma levels.

6. A method for preparing a set of fixed platelets having a predetermined level of activation, comprising:

(a) obtaining platelets from normal blood;

(b) activating the platelets to a predetermined level using a predetermined amount of an agonist;

(c) fixing the platelets using an effective amount of a fixing agent;

(d) freezing the platelets in an aqueous medium and storing the fixed platelets in frozen form prior to use; and (e) repeating steps (b) to (d) on different aliquots of the platelets using a different predetermined amount of agonist to prepare the set, wherein the predetermined amounts are selected over a range of levels suitable for generating a standard curve using the set of fixed platelets.

7. The method of claim 6, wherein the aqueous medium is a buffer solution formulated to maintain the platelets in a stable condition by maintaining salt concentrations and pH at normal plasma levels.

8. A method for preparing a set of fixed platelets having a predetermined level of activation, comprising:

(a) obtaining platelets from normal blood by separating platelets from whole blood; washing the platelets; and suspending the washed platelets in a buffer solution formulated to maintain the platelets in a stable condition by maintaining salt concentrations and pH at normal plasma levels;

(b) activating the platelets to a predetermined level using a predetermined amount of an agonist;

(c) fixing the platelets using an effective amount of a fixing agent;

(d) freezing the fixed platelets and storing the fixed platelets prior to use; and (e) repeating steps (b) to (d) on different aliquots of the platelets using a different predetermined amount of agonist to prepare the set.

9. The method of claim 8, wherein the agonist is thrombin.

10. The method of claim 8, wherein the agonist is collagen.

11. The method of claim 8, wherein the fixing agent is 1% para-formaldehyde.

12. The method of claim 8, wherein step (c) further comprises adding the fixing agent to an aqueous suspension containing the activated platelets, then centrifuging and washing the platelets.

13. In a platelet assay method which comprises determining the activation level of an unknown platelet sample, the improvement which comprises repeating the platelet assay using separate standard platelet samples each containing fixed platelets activated at different, predetermined levels to obtain standard values, and calculating the activation level of the unknown platelet sample by comparison to the assay results obtained for the standard values, wherein each standard platelet sample consists essentially of the fixed platelets and an aqueous medium in frozen form which has been thawed prior to use in the platelet assay, and the platelets of each standard have been obtained from blood, activated using a different amount of an agonist for each standard, and then fixed using an effective amount of a fixing agent.

14. The method of claim 13, wherein the step of calculating the activation level of the unknown platelet sample further comprises constructing a standard curve using the standard platelet samples.

15. The method of claim 13, wherein the aqueous medium is a platelet resuspension buffer formulated to maintain the platelets in a stable condition by maintaining salt concentrations and pH at normal plasma levels.

* * * * *